United States Patent
Yousef et al.

(10) Patent No.: US 11,077,159 B2
(45) Date of Patent: Aug. 3, 2021

(54) COMPOSITIONS FROM HALOPHYTE PLANTS AND METHODS OF USE THEREOF

(71) Applicant: KHALIFA UNIVERSITY OF SCIENCE AND TECHNOLOGY, Abu Dhabi (AE)

(72) Inventors: Lina F. Yousef, Abu Dhabi (AE); Saeed A. Alkhoori, Abu Dhabi (AE); Mette H. Thomsen, Esbjerg (DK)

(73) Assignee: KHALIFA UNIVERSITY OF SCIENCE AND TECHNOLOGY, Abu Dhabi (AE)

( * ) Notice: Subject to any disclaimer, the term of this patent is extended or adjusted under 35 U.S.C. 154(b) by 162 days.

(21) Appl. No.: 16/475,205

(22) PCT Filed: Dec. 20, 2017

(86) PCT No.: PCT/US2017/067494
§ 371 (c)(1),
(2) Date: Jul. 1, 2019

(87) PCT Pub. No.: WO2018/125694
PCT Pub. Date: Jul. 5, 2018

(65) Prior Publication Data
US 2019/0358279 A1    Nov. 28, 2019

Related U.S. Application Data

(60) Provisional application No. 62/441,350, filed on Jan. 1, 2017.

(51) Int. Cl.
| | | |
|---|---|---|
| *A61K 36/00* | (2006.01) | |
| *A61K 36/21* | (2006.01) | |
| *A61K 8/9789* | (2017.01) | |
| *A61P 17/02* | (2006.01) | |
| *A61K 9/00* | (2006.01) | |
| *A61K 36/185* | (2006.01) | |
| *A61Q 19/08* | (2006.01) | |

(52) U.S. Cl.
CPC ............ *A61K 36/21* (2013.01); *A61K 8/9789* (2017.08); *A61K 9/0014* (2013.01); *A61K 36/185* (2013.01); *A61P 17/02* (2018.01); *A61Q 19/08* (2013.01)

(58) Field of Classification Search
CPC .................................................... A61K 36/00
USPC ....................................................... 424/725
See application file for complete search history.

(56) References Cited

U.S. PATENT DOCUMENTS

| | | |
|---|---|---|
| 2012/0230930 A1 | 9/2012 | Corstjens et al. |
| 2012/0258065 A1 | 10/2012 | Dechelette et al. |

FOREIGN PATENT DOCUMENTS

| | | |
|---|---|---|
| JP | 2011006347 | 1/2011 |
| WO | 2016020339 A2 | 2/2016 |

OTHER PUBLICATIONS

Abstract for 2011-A7928, JP 2011 006347 (Univ Tsukuba) Jan. 13, 2011.
Extended European Search Report for EP Application No. 17887850.0 dated Jul. 20, 2020.
Ghazanfar, "Halophytes of Southwest Asia", Sabkha Ecosystems—vol. IV: Cash Crop Halophyte and Biodiversity Conservation, Springer Science+Business Media, Dordrecht, p. 118, Jan. 1, 2014.
Lopes, et al., "Natural products from extreme marine environments: Searching for potential industrial uses within axtremophile plants", Industrial Crops and Products 94 (2016) 299-307.
Rodrigues, et al., "Maritime Halophyte Species from Southern Portugal as Sources of Bioactive Molecules", Mar. Drugs 2014, 12, 2228-2244; doi: 10.3390/md12042228.
Singh, et al., "Notes about Haloxylon salicomicum (Moq.) Bunge ex Boiss., a promising shrub for arid regions", Gene Resour Crop Evol (2015) 62:451-463.
Donato-Trancoso A. et al, "Olive oil-induced reduction of oxidative damage and inflammation promotes wound healing of pressure ulcers in mice", Elsevier, J Dermatol Sci., 2016, vol. 83, Issue 1, pp. 60-69, 1 page.
Custodio Luisa et al, "The marine halophytes *Carpobrotus edulis* L. and *Arthrocnemum macrostachyum* L. are potential sources of nutritionally important PUFAs and metabolites with antioxidant, metal chelating and anticholinesterase inhibitory activities", Botanica Marina, 2012, vol. 55, Issue 3, pp. 281-288, 4 pages.
Poljsak Borut et al, "Skin and antioxidant", Journal of Cosmetic and Laser Therapy, 2013, vol. 15, Issue 2, pp. 107-113, 7 pages.
Khan M. Ajmal et al, "Sabkha Ecosystems", vol. IV: Cash Crop Halophyte and Biodiversity Conservation, Book, Springer, https://www.springer.com/gp/book/9789400774100, 2014, pp. 339 and 118, 3 pages.

*Primary Examiner* — Michael V Meller
(74) *Attorney, Agent, or Firm* — Billion & Armitage

(57) ABSTRACT

The invention relates to skin care compositions comprising an ethanol extract obtained from the leaves and/or stems of *Arthrocnemum macrostachyum* and/or *Tetraena* sp. cf. *mandavillei*. In addition, the invention relates to methods for treating a skin condition, reducing the risk of developing a skin condition, for treating wounds, for reducing and/or delaying the effects of aging of skin, and/or for treating and/or reducing inflammation of skin by administration of skin care compositions of the invention.

1 Claim, 4 Drawing Sheets

COMPOSITIONS FROM HALOPHYTE PLANTS AND METHODS OF USE THEREOF

STATEMENT OF PRIORITY

This application claims the benefit of International Application No. PCT/US2017/067494 filed Dec. 20, 2017 which claims the benefit of U.S. Provisional Application No. 62/441,350, filed on Jan. 1, 2017, the disclosure of which are incorporated herein by reference in their entirety.

FIELD OF INVENTION

The invention relates to skin care compositions comprising an ethanol extract from leaves and/or stems of *Arthrocnemum macrostachyum* and/or *Tetraena* sp. cf. *mandavillei* and methods for treating a skin condition and/or reducing the risk of developing a skin condition, for treating wounds, for reducing or delaying the effects of aging of skin, and for treating or reducing inflammation of skin by administration of skin care compositions of the invention.

BACKGROUND OF INVENTION

Halophyte species of the United Arab Emirates (UAE) are a source of unique active phytochemicals, potentially due to the extreme environmental conditions under which the plants grow in the UAE. Local species belonging to Aizoaceae, Amaranthaceae, Avicenniaceae, and Zygophyllaceae families have been reported to contain valuable chemicals e.g. fatty acids, terpenoids, flavonoids, alkaloids, steroids, tannins, saponins, quinones and coumarins with reported effects such as the prevention of cardiovascular diseases, as well as having anti-inflammatory, anti-carcinogenic, antioxidant, anti-microbial, anti-viral, anti-fungal, and anti-diabetic properties.

SUMMARY OF THE INVENTION

One aspect of the invention relates to a skin care composition comprising an ethanol extract from leaves and/or stems of *Arthrocnemum macrostachyum* (AM) and/or *Tetraena* sp. cf. *mandavillei* (TM), and a cosmetically acceptable carrier or a pharmaceutically acceptable carrier, wherein the extract is present in the composition in an amount from about 0.005 mg to about 0.1 mg per mL of the composition.

A further aspect of the invention relates to a method of treating a skin condition and/or reducing the risk of developing a skin condition in a subject in need thereof, comprising administering a therapeutically effective amount of a skin care composition of the invention to the skin of the subject, thereby treating the skin of the subject and/or reducing the risk of the subject developing a skin condition.

An additional aspect of the invention relates to a method of treating a wound in a subject in need thereof, comprising administering a therapeutically effective amount of the skin care composition of the invention to the wound on and/or in the subject, thereby treating the wound.

Another aspect of the invention relates to a method for reducing and/or delaying the effects of aging of skin of a subject in need thereof, comprising administering a therapeutically effective amount of the skin care composition of the invention to the skin of the subject, thereby reducing and/or delaying aging of the skin.

A further aspect of the invention relates to a method of treating and/or reducing skin inflammation of a subject in need thereof, comprising administering a therapeutically effective amount of the skin care composition of the invention to the skin of the subject, thereby treating the inflammation of the skin.

The foregoing and other aspects of the present invention will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

DETAILED DESCRIPTION

Figure 1:
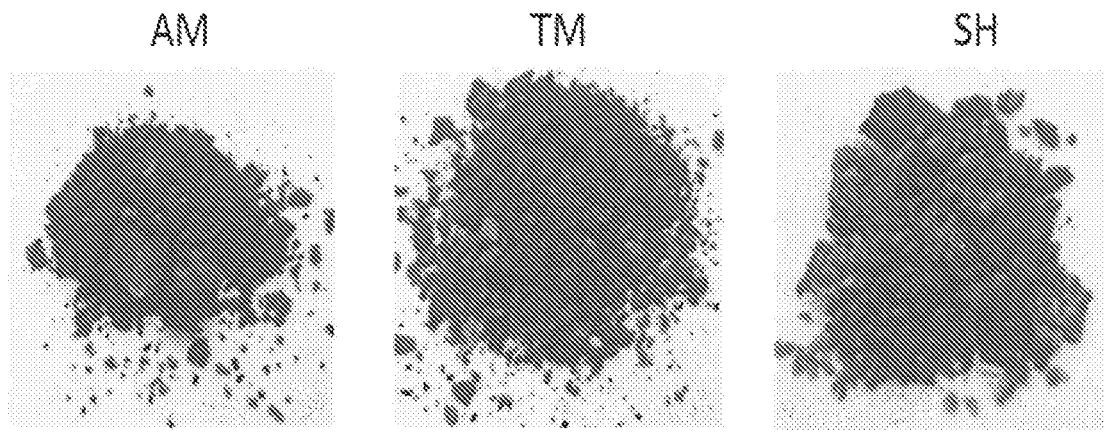
FIG. 1: Picture of (a) locally collected *Arthrocnemum macrostachyum* (b) locally collected *Tetraena* sp. cf. *mandavillei* and (c) commercially purchased *Salicornia herbacea* from desert cart.

The present invention will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount or concentration and the like, is meant to encompass variations of ±10%, ±5%, ±1%, ±0.5%, or even ±0.1% of the specified value as well as the specified value. For example, "about X" where X is the measurable value, is meant to include X as well as variations off 10%, +5%, ±1%, ±0.5%, or even 0.1% of X. A range provided herein for a measurable value may include any other range and/or individual value therein.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, the terms "increase," "increasing," "increased," "enhance," "enhanced," "enhancing," and "enhancement" (and grammatical variations thereof) describe an elevation of at least about 25%, 50%, 75%, 100%, 150%, 200%, 300%, 400%, 500% or more as compared to a control and/or a prior value.

As used herein, the terms "reduce," "reduced," "reducing," "reduction," "diminish," and "decrease" (and grammatical variations thereof), describe, for example, a decrease of at least about 5%, 10%, 15%, 20%, 25%, 35%, 50%, 75%, 80%, 85%, 90%, 95%, 97%, 98%, 99%, or 100% as compared to a control and/or a prior value. In particular embodiments, the reduction can result in no or essentially no (i.e., an insignificant amount, e.g., less than about 10% or even 5%) detectable activity or amount.

As used herein, the terms "pharmaceutically acceptable" or "cosmetically acceptable" refer to a material that is not biologically or otherwise undesirable, i.e., the material can be administered to a subject or used in contact with tissues (e.g., skin) without causing any undesirable biological effects such as toxicity incompatibility, instability, irritation, allergic response, and the like.

A "halophyte" is a plant that can grow in waters of high salinity, such as sea shores, marshes, sloughs, saline semi-deserts, and mangrove swamps. Relatively few plant species are halophytes. The halophyte "substrate" includes halophyte plant parts, such as stems and branches, which may optionally be subjected to pretreatment before digestion as taught herein.

*Arthrocnemum macrostachyum* and *Tetraena* sp. cf. *mandavillei* are halophytes found in coastal environments (e.g., salt marshes, mangroves) in most continents. To develop the seed, plants of *A. macrostachyum* and *T. mandavillei* are grown to maturity. In the initial work on this invention, these two species, *A. macrostachyum* and *T. mandavillei*, were incorrectly identified as *Salicornia* sinus *persica* and *Zygophyllum qatarense*, respectively.

Different species of halophyte biomass were selected from the United Arab Emirates to identify those that might treat and/or improve skin conditions, for example, conditions that result from exposure (e.g., wind, sun, heat, and the like) and aging. Analytical methods for identification and quantification of phytochemcials include GC-MS and LC-MS, which can be performed with two species: *A. macrostachyum* and *T. mandavillei*. Several phytochemicals with interesting properties were identified in these two species including caffeic acid, chlorogenic acid, and ferulic acid. The quantified components are strong antioxidants, with cardiovascular and antiviral effects. Other attributes included skin enhancing and skin whitening effects. Numerous other phytochemicals were identified including several strong antioxidants, and anti-inflammatory and anti-cancer components. The results showed that extractives represent a large portion of the halophyte extract but had differential amounts demonstrating that some species may provide more preferred qualities than others.

*A. macrostachyum* and *T. mandavillei* contained different levels of actives with a variety of the skin enhancing activities. *A. macrostachyum* and *T. mandavillei* were found to contain a number of phytochemicals with reported properties. However, compared to other halophyte species outside the area, the activity of extracts from *A. macrostachyum* and/or *T. mandavillei* were superior in antioxidant, antiseptic, anti-inflammatory, astringent, collagen stimulating, and skin whitening. A line of cosmetic products was developed based on high quality oils and butters mixed with the plant extracts. Tests showed that the cream developed from the extracts of these two species provided skin whitening, skin smoothing, wound healing, and/or joint-pain relieving properties.

In some embodiments, key actives were differentially extracted based on the nature of the solvent used in the extraction, e.g., water or organic (ethanol) solvents. The key actives from the leaves and stems of *Arthrocnemum macrostachyum* and *Tetraena* sp. cf. *mandavillei* were identified in ethanol extracts.

Accordingly, in some embodiments of the invention, a skin care composition is provided comprising an ethanol extract from leaves and/or stems of *Arthrocnemum macrostachyum* and/or *Tetraena* sp. cf. *mandavillei*, and a cosmetically acceptable carrier or a pharmaceutically acceptable carrier, wherein the concentration of the extract is in a range from about 0.005 mg/mL to about 0.1 mg/mL of the composition. In some embodiments, the ethanol extract is made by extracting the leaves and/or stems of *Arthrocnemum macrostachyum* and *Tetraena* sp. cf. *mandavillei* with ethanol. In some embodiments, the ethanol extract is made by extracting the leaves and/or stems of *Arthrocnemum macrostachyum* with ethanol. In some embodiments, the ethanol extract is made by extracting the leaves and/or stems of *Tetraena* sp. cf. *mandavillei* with ethanol. In some embodiments, when the extract is made from the leaves and/or stems of both *Arthrocnemum macrostachyum* and *Tetraena* sp. cf. *mandavillei*, the leaves and/or stems of the two species may be combined and extracted together or the leaves and/or stems of the two species may be extracted in the ethanol separately and then the extracts from each may be combined in any weight proportion relative to one another (e.g., 5:95, 10:90, 15:85, 20:80, 25:75, 30:70, 35:65, 40:60; 45:65, 50:50, 55:45, 60:40, 65:35; 70:30, 75:25, 80:20, 85:15, 90:10, 95:5 of *A. macrostachyum* to *T. mandavillei*, and any ratio therein).

Thus, in some embodiments, an ethanol extract of the invention comprises consists essentially of, or consists of an extract of leaves and/or stems from both *A. macrostachyum* and *T. mandavillei*. In some embodiments, an ethanol extract of the invention comprises consists essentially of, or consists of an extract of leaves and/or stems from *A. macrostachyum* only. An ethanol extract of the invention comprises consists essentially of, or consists of an extract of leaves and/or stems from *T. mandavillei* only.

In some embodiments, the concentration of an extract from the leaves and/or stems of *A. macrostachyum* and/or *T. mandavillei* present in a composition of the invention may be in a range from about 0.005 mg/mL to about 0.1 mg/mL, about 0.005 mg/mL to about 0.075 mg/mL, about 0.005 mg/mL to about 0.05 mg/mL, about 0.005 mg/mL to about 0.01 mg/mL, 0.0075 mg/mL to about 0.1 mg/mL, about 0.0075 mg/mL to about 0.075 mg/mL, about 0.0075 mg/mL to about 0.05 mg/mL, about 0.0075 mg/mL to about 0.01 mg/mL, about 0.01 mg/mL to about 0.1 mg/mL, about 0.01 mg/mL to about 0.075 mg/mL, about 0.01 mg/mL to about 0.05 mg/mL, about 0.025 mg/mL to about 0.1 mg/mL, about 0.025 mg/mL to about 0.075 mg/mL, about 0.025 mg/mL to about 0.05 mg/mL, about 0.03 mg/mL to about 0.1 mg/mL, about 0.03 mg/mL to about 0.075 mg/mL, about 0.03 mg/mL to about 0.05 mg/mL, about 0.05 mg/mL to about 0.1 mg/mL, about 0.05 mg/mL to about 0.08 mg/mL, about 0.05 mg/mL to about 0.07 mg/mL, about 0.075 mg/mL to about 0.1 mg/mL, about 0.005 mg/mL to about 0.009 mg/mL, about 0.006 mg/mL to about 0.01 mg/mL, about 0.007 mg/mL to about 0.015 mg/mL, about 0.008 mg/mL to about 0.02 mg/mL, about 0.009 mg/mL to about 0.025 mg/mL, about 0.01 mg/mL to about 0.03 mg/mL, about 0.015 mg/mL to about 0.045 mg/mL, about 0.025 mg/mL to about 0.05 mg/mL, about 0.03 mg/mL to about 0.06 mg/mL, about 0.04 mg/mL to about 0.08 mg/mL, or about 0.06 mg/mL to about 0.1 mg/mL of the composition, and any range or value therein. Thus, in some embodiments, the amount of extract in a composition of the invention may be about 0.005, 0.006, 0.007, 0.008, 0.009, 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, or 0.1 mg per mL of the composition, and any range or value therein.

In some embodiments, a skin care composition of the invention may further comprise, for example, surfactants, skin conditioning agents, abrasives, suspending aids, emollients, emulsifiers, thickening agents, absorbents, vitamins (e.g., vitamin A, vitamin E), fatty acids, sunscreens, skin lighteners, other anti-aging compounds and/or anti-wrinkle compounds, anti-cellulite compounds, other anti-inflammatory compounds, antimicrobial agents, antifungal agents, pH adjusting agents, chelating agents, buffering agents, gelling agents, antifoaming agents, buffering agents, colorants, film formers, pH adjusters, humectants, pigments, and/or any combination thereof.

In some embodiments, one or more (e.g., 1, 2, 3, 4, 5, or more) surfactants may be present in the composition. Example surfactants include, but are not limited to, amphoteric surfactants such as, e.g., cocamidopropyl betaine; anionic surfactants such as, e.g., sodium lauryl sulfoacetate; non-ionic surfactants such as, e.g., alkyl polyglucoside surfactants such as, e.g., decyl glucoside; coco-glucoside and/or glyceryl oleate; and any combination thereof In some embodiments, a surfactant may be present in the composition in an amount of about 5%, 6%, 7%, 8%, 9%, 10%, 11%, 12%, 13%, 14%, 15%, 16%, 17%, 18%, 19%, or 20% by weight of the composition. In some embodiments, the total amount of the one or more surfactants in the composition is about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, or 50% by weight of the composition.

In some embodiments, one or more (e.g., 1, 2, 3, 4, 5, or more) thickening agents may be present in the composition. Example thickening agents include, but are not limited to, acrylates copolymers, such as, e.g., those commercially available from Lubrizol under the tradename Carbopol®, e.g., Carbopol® Aqua SF-1 Polymer. In some embodiments, a thickening agent may be present in the composition in an amount of about 1%, 2%, 3%, 4%, 5%, 6%, 7%, 8%, 9%, 10%, 11%, 12%, 13%, 14%, or 15% by weight of the composition. In some embodiments, the total amount of the one or more thickening agents in the composition is about 1%, 2%, 3%, 4%, 5%, 6%, 7%, 8%, 9%, 10%, 11%, 12%, 13%, 14%, 15%, 16%, 17%, 18%, 19%, or 20% by weight of the composition.

In some embodiments, one or more (e.g., 1, 2, 3, 4, 5, or more) pH adjustment agents may be present in the composition. Example pH adjustment agents include, but are not limited to, bases such as, e.g., sodium hydroxide, potassium hydroxide, and mixtures thereof; acids such as, e.g. hydrochloric acid, citric acid, lactic acid, glycolic acid, acetic acid, and mixtures thereof; sodium carbonate; trolamine; tromethamine; aminomethyl propanol; triisopropanolamine; aminomethyl propanol; tetrahydroxypropyl ethylenediamine; tetrasodium EDTA; suttocide A; triethanolamine (e.g., Trolamine 99); and any combination thereof. In some embodiments, a pH adjustment agent may be present in the composition in an amount of about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 1.5%, 2%, 2.5%, or 3% by weight of the composition. In some embodiments, the total amount of the one or more pH adjustment agents in the composition is about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 1.5%, 2%, 2.5%, or 3% by weight of the composition.

In some embodiments, one or more (e.g., 1, 2, 3, 4, 5, or more) humectants may be present in the composition. Example humectants include, but are not limited to, polyols such as, e.g., glycerin and diols such as, e.g., propanediol; xylitylglucoside, anhydroxylitol, and/or xylitol; high hydrophile-lipophile balance (HLB), nonionic emulsifiers and emollients such as, e.g., polyethylene glycol (PEG) 45 palm kernel glycerides; sodium hyaluronate (e.g., hyaluronic acid 1%); propylene glycol; polyethylene glycol; polypropylene glycol; triethylene glycol; neopental glycols; butylene glycol; polyethylene glycol; sorbitol; arabitol; erythritol; HSH; isomalt; lactitol; maltitol; mannitol; xylitol; threitol; ribitol; galactitol; fucitol; iditol; inositol; volemitol; and any combination thereof. In some embodiments, a humectant may be present in the composition in an amount of about 0.1%, 0.5%, 1%, 1.5%, 2%, 2.5%, 3%, 3.5%, 4%, 4.5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, or 15% by weight of the composition. In some embodiments, the total amount of the one or more humectants in the composition is about 0.1%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, or 15% by weight of the composition.

In some embodiments, one or more (e.g., 1, 2, 3, 4, 5, or more) chelating agents may be present in the composition. Example chelating agents include, but are not limited to, tetrasodium salt of ethylenediaminetetraacetate (EDTA); disodium salt of EDTA; and combinations thereof. In some embodiments, a chelating agent may be present in the composition in an amount of about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 1.5%, 2%, 2.5%, or 3% by weight of the composition. In some embodiments, the total amount of the one or more chelating agents in the composition is about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 1.5%, 2%, 2.5%, or 3% by weight of the composition.

A skin care composition of the invention may comprise any cosmetically acceptable carrier or pharmaceutically acceptable carrier.

In some embodiments, a cosmetically/acceptable carrier may include, but is not limited to, water, petroleum jelly, petrolatum, mineral oil, vegetable oil, animal oil, organic and inorganic waxes, such as microcrystalline, paraffin and ozocerite wax, natural polymers, such as xanthanes, gelatin, cellulose, collagen, starch or gum arabic, synthetic polymers, alcohols, polyols, and any combination thereof.

In some embodiments, a pharmaceutically acceptable carrier may include, but is not limited to, water, glycerol, alcohol, propylene glycol, fatty alcohols, triglycerides, fatty acid esters, mineral oils, and any combination thereof.

In some embodiments, an ethanol extract of *A. macrostachyum* and/or *T. mandavillei* leaves and stems may be a liquid or it may be a solid (e.g., dried, lyophilized, etc.). In some embodiments, the extract may be a liquid or dried when it is incorporated into a composition of the invention.

In some embodiments, a skin care composition of the invention may be in the form of a solution, a liquid, a cream, a lotion, a gel, a hydrogel, an emulsion, a spray, a foam, an ointment, a paste, a plaster, a patch, tissue cloth, wipe, an aerosol, a powder (lyophilized) and/or a wound dressing textile product.

A skin care composition of the present invention may have a pH in a range of about 4 to about 9 In some embodiments, the composition may have a pH of about 4, 4.5, 5, 5.5, 6, 6.5, 7, 7.5, 8, 8.5 or 9.

In some embodiments, the invention provides methods for treating a skin condition in a subject in need thereof or reducing the risk of developing a skin condition in a subject in need thereof, comprising administering a therapeutically effective amount of the skin care composition of the invention to the skin of the subject. Without being bound by theory, it is believed that skin conditions treated with the compositions of the invention are improved when administered the compositions of the invention (as compared to skin conditions not treated with the compositions of the invention) through the ability of the compositions to, for example, inhibit oxidation in the skin.

In some embodiments, the skin condition may be wrinkles and/or fine lines due to aging and the composition is applied to the fine line and/or wrinkle and/or to an area on the subject's skin where it is believed a fine line and/or wrinkle may develop, thereby treating or reducing the risk of developing fine lines and/or wrinkles. In some embodiments, administration of a composition of the invention to the skin of a subject reduces fine lines and/or wrinkles in the subject as compared to a subject not receiving such treatment.

In some embodiments, the skin condition may be erythemic skin and the composition is applied to the erythemic skin and/or to an area on the subject's skin where it is believed erythema skin may develop, thereby treating and/or reducing the risk of developing erythema on the skin. In some embodiments, administration of a composition of the invention to the skin of a subject reduces erythemic skin and/or the risk of developing erythema in the subject as compared to a subject not receiving such treatment.

In some embodiments, the skin condition may be dry, flaky, and/and/or itchy skin and the composition is applied to the dry, flaky, and/and/or itchy skin or to an area on the subject's skin where it is believed dry, flaky, and/and/or itchy skin may develop, thereby treating or reducing the risk of developing dry, flaky, and/or itchy skin. In some embodiments, administration of a composition of the invention to the skin of a subject reduces dry, flaky, and/or itchy skin or the risk of developing dry, flaky, and/or itchy in the subject as compared to a subject not receiving such treatment.

In some embodiments, the skin condition may be melasma and/or skin having an uneven tone and the composition is applied to the melasma and/or skin having an uneven tone or to an area on the subject's skin where it is believed melasma and/or uneven tone may develop, thereby treating or reducing the risk of developing melasma and/or an uneven tone on the skin. In some embodiments, administration of a composition of the invention to the skin of a subject reduces melasma and/or skin having an uneven tone or the risk of the subject developing melasma and/or skin having an uneven tone as compared to a subject not receiving such treatment.

In some embodiments, a method for reducing and/or delaying the effects of aging of skin of a subject is provided, the method comprising administering a therapeutically effective amount of a skin care composition of the invention to the skin of the subject, thereby reducing and/or delaying aging of the skin. In some embodiments, "the effects of aging" may be frown wrinkles, forehead wrinkles, crow's feet, and/or nose crease wrinkles. In some embodiments, the composition comprises extracts of *A. macrostachyum* and *T. mandavillei*. In some embodiments, the extract in the composition is from *A. macrostachyum* only.

In some embodiments, administration of a composition of the invention to the skin of a subject reduces the effects of aging as compared to a subject not receiving such treatment. Without being bound by theory, it is believed that the anti-aging effects of the compositions of the invention may be the result of the ability of the compositions to inhibit matrix metalloproteinases (MMP1) release. MMP1 is a collagenase that breaks down collagen. By inhibiting MMP1, the breakdown of collagen is reduced/delayed/prevented. By preserving natural collagen levels in the skin, the effects of aging (such as wrinkles, crows feet and the like) may be reduced/delayed/prevented.

In some embodiments, administration of a composition of the invention on the skin of a subject, may reduce MMP1 release by about 30% to about 50% (e.g., about 30, 31, 32, 33, 34, 35, 36, 37, 38, 39, 40, 41, 42, 43, 44, 45, 46, 47, 48, 49, 50%) compared to the skin of a subject that has not been administered the composition. In some embodiments, the administration of a composition of the invention on the skin of a subject, reduces MMP1 release by about 40% as compared to a subject that has not been administered the composition.

In some embodiments, a method of treating inflammation of the skin of a subject, is provided comprising administering a therapeutically effective amount of a skin care composition of the invention to the skin of the subject, thereby treating the inflammation of the skin. In some embodiments, administration of a composition of the invention to the skin of a subject reduces skin inflammation as compared to a subject not receiving such treatment.

In some embodiments, administration to the skin of a subject for treating a condition, for reducing and/or delaying the effects of aging of skin, and/or for treating and/or reducing skin inflammation may be topical or dermal. The present invention envisions the use of any method of dermal or topical application of a composition of the invention to the skin. In some embodiments, a composition of the invention may be administered to the skin by injection, spray, aerosol, towel, sponge, and/or may be applied directly by hand. In some embodiments, a composition of the invention may be administered to the skin using patches or bandages.

A composition of the invention may also be used to treat wounds. Thus, in some embodiments, a method of treating a wound in and/or on a subject in need thereof is provided, comprising administering a therapeutically effective amount of a skin care composition of the invention to the wound in and/or on the subject, thereby treating the wound. Any wound may be treated with a composition of the invention. Non-limiting examples of wounds that may be effectively treated with a composition of the invention include a surgical site, a trauma site, a burn, an abrasion, a sunburn, an ulcer, a cut, and/or laceration. In some embodiments an ulcer may be treated, including, but not limited to, a skin ulcer, a vasculitic ulcer, a venous ulcer or a venous stasis ulcer, an arterial ulcer, a pressure ulcer or a decubitus ulcer, and/or a diabetic ulcer.

When treating a wound, a composition of the invention may be applied in any manner suitable for the particular would. For example, the composition may be applied topically or dermally. In some embodiments, a composition may be applied in a patch and/or in/on a bandage and/or dressing. In some embodiments, a composition of the invention may be administered to the wound by injection, spray, aerosol, towel, sponge, and/or may be applied directly by hand.

The invention will now be described with reference to the following examples. It should be appreciated that these examples are not intended to limit the scope of the claims to the invention, but are rather intended to be exemplary of certain embodiments. Any variations in the exemplified methods that occur to the skilled artisan are intended to fall within the scope of the invention.

EXAMPLES

Example 1: Fractionation and Separation Processes to Obtain Chemicals, Protein, and Sugars from Halophytes Chemical characterization of the extracts focused on identifying the active components using primarily high-performance liquid chromatography (HPLC) and gas chromatography (GC). HPLC is the most sensitive and extensively used method, which can separate many different chemicals e.g. carotenoids, bioflavonoids, alkaloids, catechins or sterols. Flavonoids such as quercetin and isorhamnetin along with chlorogenic acid have been reported to be quantified by reversed-phased HPLC (RP-HPLC) with an MS, UV (or a DAD) detector (at 340, 350 and 370 nm) using $C_{18}$ (ODS) columns and three types of mobile phases: aqueous solution of orthophosphoric acid with methanol or acetonitrile, or formic acid with acetonitrile (depending on the analyzed compound and method described). Alkaloids and catechins have been analyzed using HPLC-UV (at 280 nm), with an Inertsil ODS column and phosphate-acetonitrile mobile phase. HPLC-MS and GC-MS have also been extensively applied to pharmaceutical grade analysis e.g. fatty acids, terpenes, sterols, alkaloids, flavonoids and many more, however, most of these compounds need derivatization prior to the analysis. Fatty acids e.g. palmitic, oleic, or linoleic acids have been reported to be quantified (as FAME) using a DB-1 column coated with a dimethyl polysiloxane film or a TG-5 (ThermoScientific) fused silica capillary column, with helium as the carrier gas and EI (electron impact) ionization mode in the MS detector. GC-FID was also used for the detection of these fatty acids methyl esters using a DB-17 capillary column or a CP-Sil-8-CB column and with nitrogen gas as a carrier. Alkaloids have been reported to be analyzed by GC with a triple quadruple MS detector using e.g. HP1-MS capillary column or DB-1701 capillary column with helium as a carrier gas. Flavonoids were quantified with GC-MS, using e.g. OV-1 capillary column with helium as a carrier gas or LC-MS using LiChrospher RP $C_{18}$ column with water, acetic acid, acetonitrile mobile phase and with electrospray chemical ionization mode of the MS detection, which eliminates the need for derivatization of the compounds to make them volatile. Chemical characterization of biomass macronutrients (carbohydrates, protein, lignin) was performed using acid hydrolysis followed by standard HPLC.

In this example, for extraction of phytochemicals, one gram of the halophyte plant species, *Arthrocnemum macrostachyum* (AM) biomass was subjected to extraction in 100 gram of either an organic solvent (ethanol) or a water extraction using a traditional Soxhlet apparatus for 12 hours per solvent. The number of refluxes were two hour reflux with water and five hour reflux with ethanol. Each solvent was evaporated and the concentrated extracts were dried at 50° C. in the drying oven. Dried extracts have been stored at 4° C. until analyzed.

The mass balance of the extraction process is shown in Table 1. The water extractives value includes extractable ash of the plant.

TABLE 1

| Extract content of AM | |
|---|---|
| Extraction solvent | AM |
| Water [g/100 g DM] | 37.79 |
| Ethanol [g/100 g DM] | 8.82 |

Example 2: Quantitative Analysis of AM Extracts

LC analysis was performed using the UltiMate 3000 RSLC chromatographic equipped with a Luna 3 um C18 (2) 100 A (150 mm×2.0 mm×3 um) column and coupled with a API 4000 QTRAP triple quadrupole mass spectrometer. The Turbo Ion Spray source operated in negative ion mode. Mobile phase used was composed of 5 mM $AcNH_4$ (A) and ACN (B) in a gradient increasing B component from 10 to 100%. Samples were analyzed using standard addition method for three phenolic acids: chlorogenic, caffeic and ferulic acid, based on preliminary identification. Dry extracts were dissolved in water and spiked with all three standards at different concentrations.

Three phenolic acids have been identified and quantified using the standard addition method; chlorogenic acid, caffeic acid, and ferulic acid.

Chlorogenic acid is present in abundance in many plants and considered an antioxidant, having a stronger activity than e.g. ascorbic acid, tocopherol or beta-carotene, and has a protective effect on rat cardiomyocytes, suggesting its application in preventing cardiovascular disease. Caffeic acid, possessing similar properties to chlorogenic acid. Ferulic acid, described in previous section. The quantitative results of the plants analyzed is presented in Table 2.

TABLE 2

Content of chlorogenic, caffeic and ferulic acids in water and ethanol extracts obtained from AM

| Sample AM | Caffeic acid per dry extract [mg/100 g] | Chlorogenic acid per dry extract [mg/100 g] | Ferulic acid per dry extract [mg/100 g] |
|---|---|---|---|
| Water Extract | 6.8 | 20.52 | 27.08 |
| Ethanol Extract | 0.22 | 10.70 | 6.55 |

Chlorogenic and ferulic acids have been found in significant amounts in the water extracts from both plants. This shows that polar solvents are probably better suited for the extraction of these compounds. Extraction with polar organic solvents are used to minimize the influence of ash present in high amounts in the water extracts.

Example 3: Efficacy of Plant Extracts from AM for Skin Treatment

The extracts from AM were tested for skin enhancing properties.

A cream was produced from natural oils and butters using either 2% or 5% volume/volume of the extract added. The cream was applied to the skin of several subjects and found to have exceptional properties such as skin healing, skin whitening and smoothing, and joint-pain relieving.

For example, the effect on skin healing was examined in a subject having had knee surgery. Within 3 months after surgery the scar was still red and irritated; however, after applying the cream for 2-3 weeks the scar got significantly less red and irritated and the itchiness disappeared. In addition, arthritic pain in the knee was relieved.

Example 4: Botanical Extracts of AM and TM Compared to *Salicornia herbacae*

Botanical extracts from UAE native *Tetraena* sp. cf. *mandavillei* (TM) and two *Salicornia* species, one that is native to the UAE (*Arthrocnemum macrostachyum* (AM)) and the other originating from South Korea (*Salicornia herbacea*) (SH) were prepared using soxhlet extraction with 50% absolute ethanol (v/v). *Salicornia herbacae* is reported to be present in skin and cosmetics for the treatment of anti-aging, whitening, and disease related skin problems.

Whole plants of AM (FIG. 1 (panel a)) and TM (FIG. 1 (panel b)) were collected from Abu Dhabi, UAE in early August 2016 (Table 3). The identity of the plants was established by geographic range known for these plants and morphological characterization, which were also confirmed by a horticultural expert. Dry whole plants of SH were purchased online from desertcart, and are imported from a vendor in South Korea, where it is locally known as Ham Cho herbacea (FIG. 1 (panel c)). Freshly collected AM and TM plants were immediately dried upon collection at 80° C. for 24 hours and stored at 22° C. along with SH until phytochemical extraction. Gallic acid, L-ascorbic acid, Folin-Ciocalteu phenol, sodium carbonate 2,2-diphenyl-1-picryhydrazyl (DPPH) and solvents (absolute ethanol, methanol) were of analytical grade and purchased from Sigma Aldrich (USA).

TABLE 3

Plants and geographic location of collection sites.

| Plant | Common name | Area | Coordinate |
|---|---|---|---|
| AM | Ramth (رمث) | Al Maqtaa (Bain AlJesrain) | 24°23'56"N 54°30'29"E |
| TM | Harm (هرم) | Khalifa City | 24°25'33"N 54°32'35"E |

Figure 2:
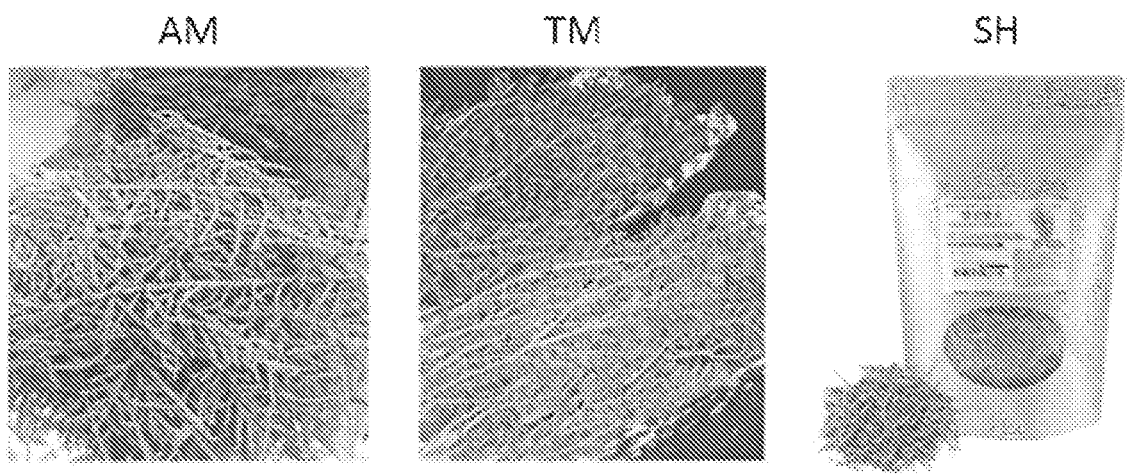
FIG. 2: Picture of dried botanical extracts collected after Soxhlet extraction and drying at 105° C. in a convention oven: (a) locally collected *Arthrocnemum macrostachyum* (b) locally collected *Tetraena* sp. cf. *mandavillei* and (c) commercially purchased *Salicornia herbacae*.

Dry AM, TM and SH biomass were milled to a fine powder using a household coffee bean grinder. Three grams from each of the dried plant powder were extracted for eight hours with 100 mL of 50% absolute ethanol (v/v) using a Soxhlet extractor over 8 hours at 100° C. The ethanol extracts were then transferred to ceramic crucibles and dried at 105° C. for 12 hours in a conventional oven to remove the solvent. The dried botanical extracts were collected (FIG. 2) and stored at −20° C. until further analysis. The visible absorbance spectra in the range of 300-800 nm were determined for botanical extracts (1 mg/mL) dissolved in 50% ethanol (v/v). All extractions were carried out in triplicate. Extraction yield and extraction residue were calculated as follows:

(%)=(EY or ER/Biomass)*100

Where; EY is weight of the botanical extract after drying at 105° C. in the oven; ER is the weight of residual biomass remaining in the thimble after Soxhlet extraction: Biomass is the weight of initial powdered plant material used in the extraction.

The total phenolic content (TPC) of botanical extracts were determined using the Folin-Ciocalteu phenol reagent similar to the method reported in Singh et al. The assay consisted of 0.5 mL of 1 mg/mL botanical extracts dissolved in methanol, 2.5 mL 10% of Folin-Ciocalteu reagent in water and 2 mL 7.5% sodium carbonate solution. After 1 hour of reaction time in the dark at room temperature, the absorbance at 765 nm was measured and used to calculate TPC using Gallic acid as standard. TPC of botanical extracts were expressed as mg Gallic Acid Equivalents (GAE)/g dry botanical extract.

Example 5: Comparison of Adical DPPH Scavenging Activity (Antioxidant Activity) of Botanical Extracts of TM, AM and SH The free radical scavenging capacity of AM, TM and SH extracts were measured using DPPH (sodium carbonate 2,2-diphenyl-1-picryhydrazyl) in a 3.8 mL assay by the method of Blois. In brief, 0.5 mM solution of DPPH was prepared in methanol, and 0.3 mL of this solution was added to 3 mL of methanol and 0.5 mL of test extract dissolved in 50% ethanol (v/v) to achieve final test extract concentrations of 0.03 to 0.66 mg/mL. After 20 minutes at room temperature in the dark, absorbance was measured at 517 nm and corrected against a blank containing 3.3 mL methanol and 0.5 mL 50% ethanol (v/v). Two controls were used in the DPPH assay; a negative control containing all reagents except for the test extract, and a positive control using a final concentration of 0.33 mg/mL L-ascorbic acid as antioxidant instead of test extract. Radical scavenging activity was calculated as follows:

Scavenging activity (%)=[$(A_{control}-A_{test})$/$A$test]*100

Where $A_{control}$ is the negative control (without test extract), and $A_{test}$ is the absorbance with the botanical extract. All analysis were carried out in triplicate.

Figure 4:
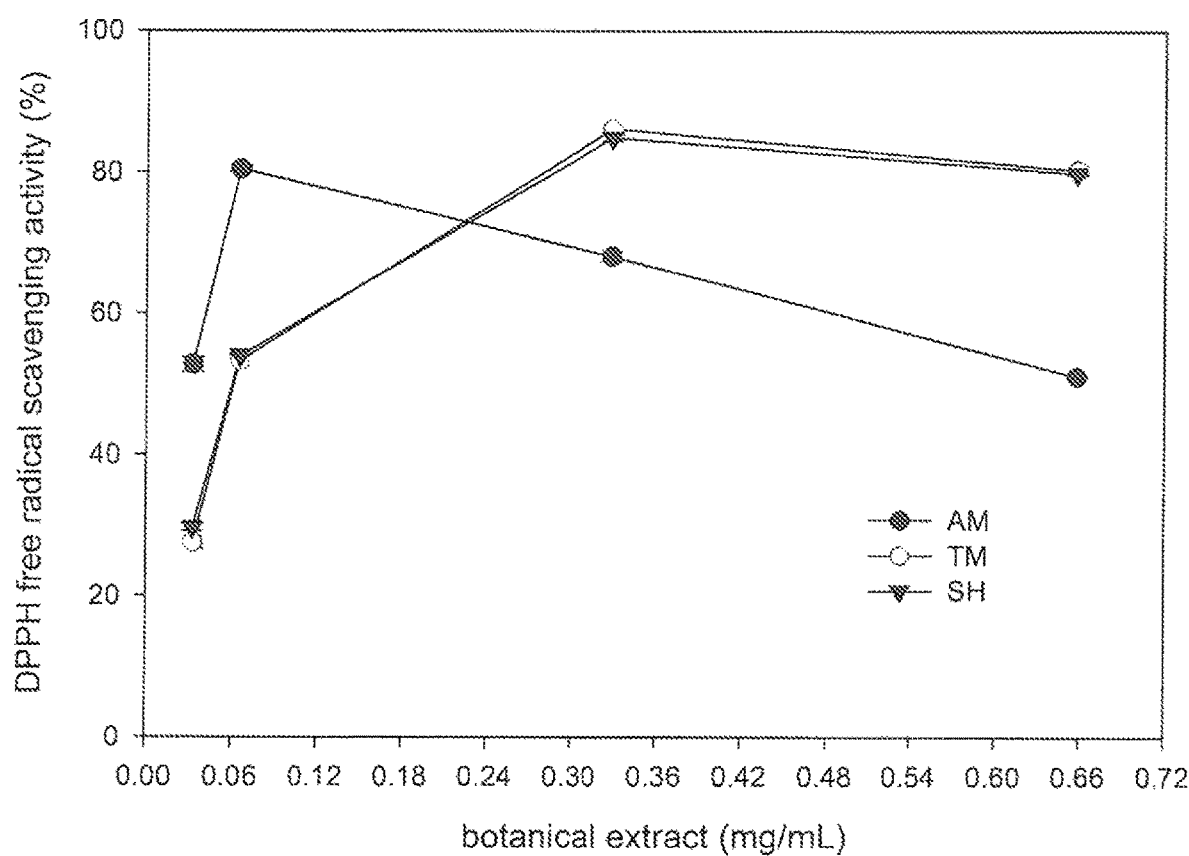
FIG. 4: Antioxidant activity of botanical extracts at different concentrations ranging from 0.03 to 0.66 mg/mL using the DPPH assay.

The DPPH free radical scavenging activity (antioxidant activity) of botanical extracts when examined using a concentration range of 0.03-0.66 mg/mL is shown in FIG. 4. L-ascorbic acid (0.3 mg/mL) showed 95.79±0.17% DPPH scavenging activity under the assay conditions used in this study. Values are the average of three independent assays±standard errors.

The DPPH scavenging activity profile of AM is different compared to TM and SH, both of which appear to behave the same. Specifically, AM extract exhibited higher DPPH scavenging activity (~55% and ~80%) when assayed at concentrations of 0.03 and 0.06 mg/mL compared to the other two botanical extracts which had substantially lower DPPH scavenging activity when assayed at these same concentrations (~30% and ~55%). The extract concentration at which the highest DPPH scavenging activity was observed is 0.06 mg/mL for AM (~80%), whereas it is 0.33 mg/mL for both TM and SH (~85%).

Example 6: Yield, Residue, Total Phenolic Content (TPC) and Absorbance Spectra

Fibroblasts and keratinocytes were seeded in 96-well plates and cultured in culture medium (DMEM or K-SFM, respectively) for 24 hours. The medium was then replaced by assay medium containing or not (control) the botanical extracts and the cells were incubated for 72 hours. At the end of the treatment, the cell viability was assessed using a classical MTT reduction assay.

Botanical extracts were evaluated for anti-aging, cell renewal and anti-inflammatory properties via systemic application (diluted in the culture medium) using the concentrations that were determined not toxic for skin cells (0.1 mg/ml) followed by two successive 3-fold dilutions. The matrix metalloproteinase-1 (MMP-1) assay using a specific ELISA kit was used to evaluate anti-aging properties. The migration/proliferation of NHEK using kinetic image analysis of the wound recovery was used to evaluate cell renewal properties. The IL-8 release on NHEK stimulated by PMA using a specific ELISA kit was used to evaluate anti-inflammatory properties.

Figure 3:
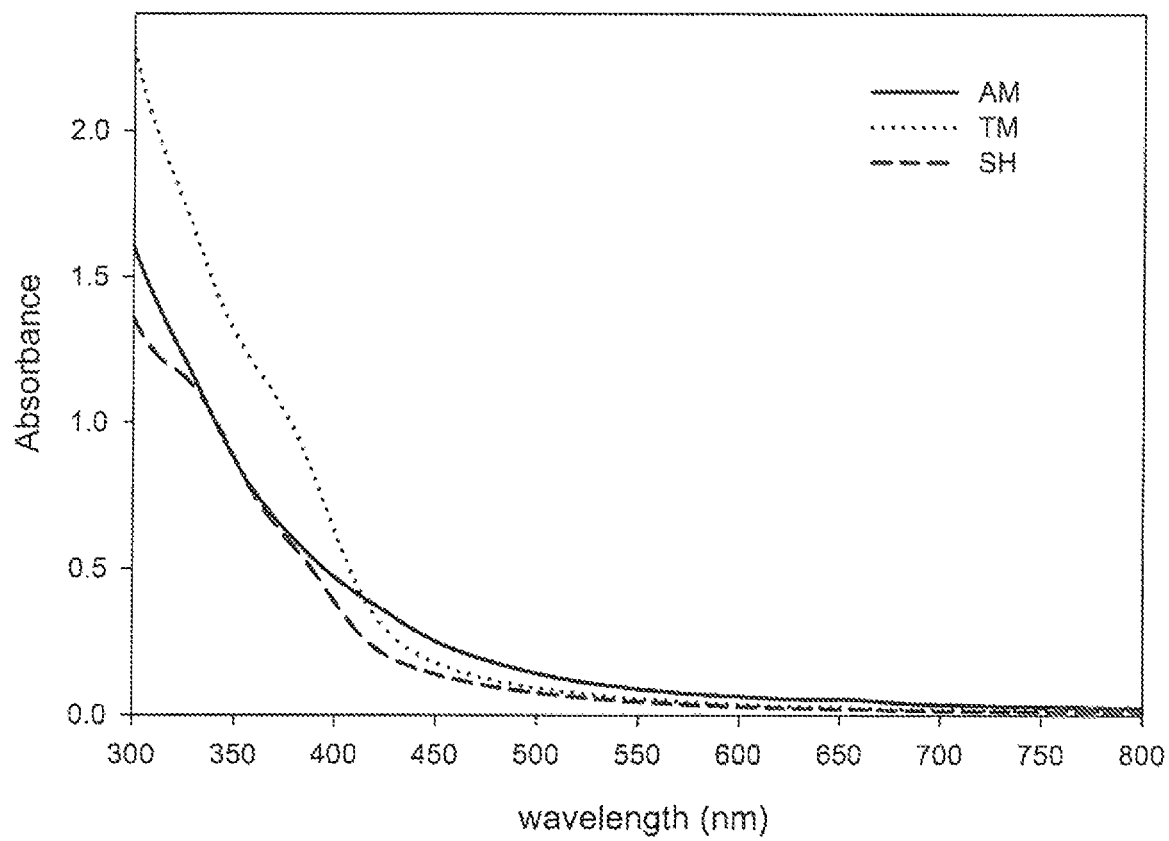
FIG. 3: Absorption spectra of botanical extracts (1 mg/mL) dissolved in 50% ethanol (v/v).

The extraction yield (botanical extract from Soxhlet extraction), extraction residue (biomass remaining in thimble after Soxhlet extraction) and TPC of botanical extracts for AM, TM and SH are shown in Table 5. Extraction yields appear to be similar for all plants but AM and SH have slightly higher yields (~35% or 0.35 g extract/g biomass) than TM (31% or 0.31 g extract/g biomass). The TPC is highest for TM (~47 mg GAE/g extract) followed by AM (~41 mg GAE/g extract). SH exhibited the lowest TPC (~32 mg GAE/g extract). The extraction residue is highest for SH (~50%) followed by AM (~41%) and TM (~38%). The absorbance spectra (300-800 nm) of botanical extracts (1 mg/mL) is shown in FIG. 3. The spectral profile of botanical extracts are different from each other, but all extracts appear to have higher absorbance measurements in the 300-420 nm. Differences in the spectral profile of botanical extracts suggests the chemical composition of the extracts are different from each other.

TABLE 4

Extraction yield, extraction residue, and total phenolic content (TPC) of the botanical extracts. Values reported averages of three independent analysis ± standard error.

| Plant | extraction yield (% weight) | extraction residue (% weight) | TPC (mg GAE*/g) |
|---|---|---|---|
| AM | 35.07 ± 0.20 | 41.06 ± 0.12 | 40.97 ± 0.98 |
| TM | 31.44 ± 0.47 | 37.89 ± 0.53 | 47.01 ± 0.63 |
| SH | 35.48 ± 0.16 | 50.40 ± 0.46 | 32.23 ± 1.34 |

*Gallic acid equivalent

Botanical extracts demonstrated differences in their total phenolic content (Table 5) and visible absorbance spectra (FIG. 4) suggesting differences in their chemical composition. The botanical extract derived from AM showed a different DPPH free radical scavenging activity (antioxidant activity) profile when compared to botanical extracts of TM or SH; both of which appear to behave similarly (FIG. 3). Specifically, the AM extract exhibited higher DPPH scavenging activity (~55% and ~80%) when assayed at concentrations of 0.03 and 0.06 mg/mL compared to TM or SH, which had substantially lower DPPH scavenging activity when assayed at these same concentrations (~30% and ~55%). The extract concentration at which the highest DPPH scavenging activity was observed is 0.06 mg/mL for AM (~80%), whereas the highest DPPH scavenging activity for TM and SH extracts was 0.33 mg/mL for both TM and SH (~85%). Collectively, the results suggest that the chemical composition of botanical extracts are different from each other, but botanical extracts derived from AM appears to be about 6-fold more active than extracts from TM or SH.

Example 7. Toxicity, MMP-1 Release, Release of IL-8, and Migration of Keratinocytes All three botanical extracts exhibited similar cell toxicity with a non-toxic threshold of 1 mg/mL (Table 5 and Table 6). Specifically, the extracts were determined to be safe on human epidermis (fibroblasts and keratinocytes) at all tested concentration (0.011, 0.033, and 0.1 mg/ml).

In vitro cell assays showed that AM presented a significant concentration-dependent inhibitory effect on MMP-1 release by aged fibroblasts at concentrations of 0.033 and 0.1 mg/mL (Table 7). Therefore, suggesting that AM could protect the extracellular matrix against degradation and provide an anti-aging effect when applied to skin.

In addition, botanical extracts of AM of 0.1 mg/ml moderately but significantly decreased the release of IL-8 by stimulated NHEK at a concentration of 0.1 mg/mL (Table 8), thereby showing the anti-inflammatory properties of AM. Phorbol myristate acetate (PMA) was used an inflammatory inducer, staurosporine was used as a control for skin inflammation and it inhibited interleukin-8 release by 50%. At concentration of 0.1 mg/ml, TM and AM extracts exhibited a similar anti-inflammation effect.

Figure 5:
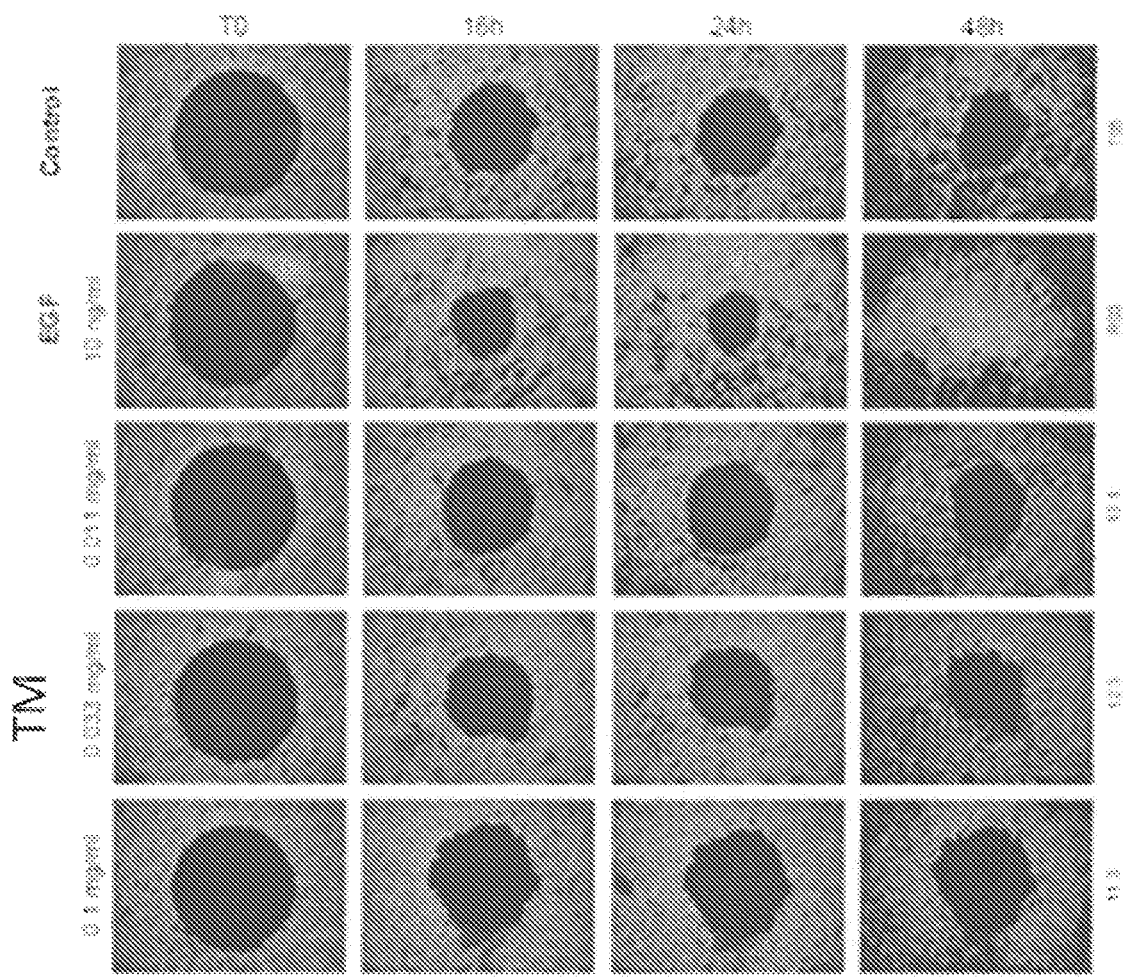
FIG. 5: Migration assay microscopic images for *Tetraena* sp. cf. *mandavillei* botanical extract.

Furthermore, the AM botanical extract significantly stimulated the migration of keratinocytes at concentrations as low as 0.011 mg/mL (Table 9 and FIG. 5); demonstrating an improvement of wound healing after treatment with the botanical extract when compared to extracts of S. herbacae.

Both AM AND TM botanical extracts showed significant wound healing ability at all tested concentrations. As shown in Table 10, the healing ability is dose-dependent for extracts from both AM and TM. Wound healing activity of extracts decreases with increase in concentration. Wound recovery using the control (EGF) at a concentration of 10 ng/ml and incubation time of 16, 24, and 48 hours was 74%, 82%, and 100%, respectively.

Example 8. Hyaluronic Acid Synthesis

As shown in Table 11, the AM botanical extract exhibited a weak release of hyaluronic acid with a dose dependent effect; 0.011, 0.033, and 0.1 mg/ml stimulated 8, 12, and 15% of hyaluronic acid, respectively. This is compared to the control, retinoic acid, which stimulated 141% of hyaluronic acid.

Example 9. Scavenging of Reactive Oxygen Species

Further, the AM extracts showed scavenging of reactive oxygen species (at the highest tested concentration of 0.1 mg/ml). At this concentration, the extract scavenged 19% while the control reference (Vitamin-E) scavenged 92% of ROS.

TABLE 5

Comparison of normal human epidermal keratinocytes cytotoxicity in vitro of AM. TM and SH extracts. The darkened line at 0.1 signifies the toxicity threshold.

| | Control | | 0.00046 | 0.0014 | 0.0041 | 0.012 | 0.037 | Unit: mg/ml 0.1 0.111 | 0.333 | 1 |
|---|---|---|---|---|---|---|---|---|---|---|
| | | | | | AM | | | | | |
| Viability (%) | 98 | 102 | 94 | 90 | 91 | 82 | 71 | 65 | 59 | 50 |
| | 102 | 95 | 93 | 95 | 93 | 82 | 71 | 59 | 56 | 51 |
| | 106 | 96 | 97 | 95 | 87 | 76 | 70 | 58 | 56 | 50 |
| Mean | 100 | | 95 | 93 | 90 | 80 | 71 | 61 | 57 | 50 |
| sem | 2 | | 1 | 2 | 2 | 2 | 0 | 2 | 1 | 1 |
| Morphological observations | + | | + | + | + | + | + | + | +/−, g | +/−, g |
| | | | | | TM | | | | | |
| Viability (%) | 101 | 96 | 95 | 93 | 95 | 97 | 96 | 97 | 99 | 113 |
| | 104 | 97 | 96 | 94 | 95 | 95 | 99 | 98 | 100 | 113 |
| | 106 | 96 | 100 | 93 | 98 | 100 | 104 | 100 | 108 | 111 |
| Mean | 100 | | 97 | 93 | 96 | 97 | 99 | 98 | 102 | 112 |
| sem | 2 | | 2 | 0 | 1 | 1 | 2 | 1 | 3 | 1 |
| Morphological observations | + | | + | + | + | + | + | + | +, g, * | +, g, * |
| | | | | | SH | | | | | |
| Viability (%) | 100 | 99 | 101 | 96 | 94 | 98 | 98 | 95 | 69 | 96 |
| | 103 | 94 | 98 | 95 | 99 | 98 | 95 | 95 | 93 | 94 |
| | 102 | 102 | 106 | 107 | 104 | 102 | 102 | 99 | 95 | 98 |
| Mean | 100 | | 102 | 99 | 99 | 100 | 98 | 97 | 86 | 96 |
| sem | 1 | | 2 | 4 | 3 | 1 | 2 | 1 | 8 | 1 |
| Morphological observations | + | | + | + | + | + | + | + | +, g, * | +, g, * |

+: normal population;
+/−: growth reduction;
−: toxicity;
0: cell mortality
g: grains of compound;
op: opacity of the compound;
*: morphological modification;
ag: agglutinated cells
sem: Standard error of the mean (standard deviation divided by sample size square root)

TABLE 6

Normal human dermal fibroblast cytotoxicity of AM, TM and SH extracts.
The darkened line at 0.1 indicates the toxicity threshold.

Unit: mg/ml

|  | Control | 0.00046 | 0.0014 | 0.0041 | 0.012 | 0.037 | 0.111 | 0.333 | 1 |
|---|---|---|---|---|---|---|---|---|---|
| AM | | | | | | | | | |
| Viability (%) | 90  89 | 87 | 88 | 87 | 80 | 77 | 70 | 55 | 6 |
|  | 109  109 | 107 | 103 | 103 | 93 | 83 | 77 | 67 | 7 |
|  | 98  106 | 102 | 100 | 98 | 104 | 78 | 71 | 62 | 8 |
| Mean | 100 | 99 | 97 | 96 | 92 | 79 | 73 | 61 | 7 |
| sem | 4 | 6 | 5 | 5 | 7 | 2 | 2 | 3 | 1 |
| Morphological observations | + | + | + | + | + | + | + | +/−, g, * | −, g |
| TM | | | | | | | | | |
| Viability (%) | 88  100 | 98 | 88 | 96 | 93 | 94 | 94 | 93 | 67 |
|  | 112  109 | 105 | 110 | 108 | 108 | 102 | 111 | 107 | 76 |
|  | 96  95 | 102 | 101 | 98 | 102 | 104 | 111 | 110 | 75 |
| Mean | 100 | 102 | 100 | 101 | 101 | 100 | 105 | 103 | 73 |
| sem | 4 | 2 | 6 | 4 | 4 | 3 | 6 | 5 | 3 |
| Morphological observations | + | + | + | + | + | + | + | +, *, g | +/−, *, g |
| SH | | | | | | | | | |
| Viability (%) | 107  92 | 103 | 107 | 102 | 96 | 96 | 90 | 85 | 4 |
|  | 106  94 | 103 | 96 | 97 | 98 | 94 | 88 | 90 | 5 |
|  | 100  101 | 99 | 102 | 104 | 98 | 102 | 96 | 89 | 6 |
| Mean | 100 | 102 | 102 | 101 | 97 | 98 | 91 | 88 | 5 |
| sem | 2 | 1 | 3 | 2 | 1 | 2 | 2 | 2 | 1 |
| Morphological observations | + | + | + | + | + | + | + | +/−, * | −, g, * |

+: normal population;
+/−: growth reduction;
−: toxicity;
0: cell mortality
g: grains of compound;
op: opacity of the compound;
*: morphological modification;
ag: agglutinated cells
sem: Standard error of the mean (standard deviation divided by sample size square root)

TABLE 7

Evaluation of matrix metalloproteinase-1 (MMP-1) release and anti-aging properties of AM, TM and SH extracts.

| Treatment | | MMP-1 (ng/ml) dilution factor adjusted | Mean (ng/ml) | sem (ng/ml) | % Control (P17-F) (%) | sem | $p^{(1)}$ | Normalized data % Inhibition (%) | sem | $p^{(1)}$ |
|---|---|---|---|---|---|---|---|---|---|---|
| Test compound | Concentration | | | | | | | | | |
| P7-NHDF Control | — | 4.8  4.9  5.1 | 4.9 | 0.1 | 34 | 1 | ** | 66 | 1 | ** |
| P17-F Control | — | 14.7  16.7  12.4 | 14.6 | 1.2 | 100 | 8 | — | 0 | 8 | — |
| Dexamethasone | $10^{-7}$M | 8.7  8.2  8.5 | 8.5 | 0.2 | 58 | 2 | nc | 42 | 2 | nc |
| AM | 0.011 mg/ml | 10.8  13.0  14.9 | 12.9 | 1.2 | 88 | 8 | ns | 12 | 8 | ns |
|  | 0.033 mg/ml | 9.1  10.3  8.7 | 9.4 | 0.5 | 64 | 3 | * | 36 | 3 | * |
|  | 0.1 mg/ml | 7.3  9.5  8.2 | 8.3 | 0.6 | 57 | 4 | * | 43 | 4 | * |

TABLE 7-continued

Evaluation of matrix metalloproteinase-1 (MMP-1) release and anti-aging properties of AM, TM and SH extracts.

| Treatment | | Basic data | | | | | | Normalized data | | |
|---|---|---|---|---|---|---|---|---|---|---|
| | | MMP-1 (ng/ml) dilution factor adjusted | Mean (ng/ml) | sem (ng/ml) | % Control (P17-F) (%) | sem (%) | p[(1)] | % Inhibition | sem (%) | p[(1)] |
| Test compound | Concentration | | | | | | | | | |
| TM | 0.011 mg/ml | 14.9<br>16.4<br>15.3 | 15.5 | 0.4 | 106 | 3 | ns | −6 | 3 | ns |
| | 0.033 mg/ml | 14.2<br>16.8<br>16.0 | 15.7 | 0.8 | 107 | 5 | ns | −7 | 5 | ns |
| | 0.1 mg/ml | 15.6<br>17.0<br>16.9 | 16.5 | 0.5 | 113 | 3 | ns | −13 | 3 | ns |
| SH | 0.011 mg/ml | 11.1<br>12.0<br>11.1 | 11.4 | 0.3 | 78 | 2 | ns | 22 | 2 | ns |
| | 0.033 mg/ml | 11.7<br>12.7<br>12.1 | 12.2 | 0.3 | 83 | 2 | ns | 17 | 2 | ns |
| | 0.1 mg/ml | 12.2<br>11.1<br>9.1 | 10.8 | 0.9 | 74 | 6 | ns | 26 | 6 | ns |

[(1)]Threshold for statistical significance
*: 0.01 to 0.05, Significant
ns: >0.05, Not significant
**: 0.001 to 0.01, Very significant
***: <0.001, Extremely significant

TABLE 8

Evaluation of anti-inflammatory properties through IL-8 release of NHEK stimulated by PMA of AM, TM and SH extracts.

| Treatment | | | Basic data | | | | | Normalized data | | |
|---|---|---|---|---|---|---|---|---|---|---|
| Test compound | | Concentration | IL-8 (pg/ml) dilution factor adjusted | Mean (pg/ml) | sem (pg/ml) | % Stimulated control | sem (%) | p[(1)] | % Inhibition | sem (%) | p[(1)] |
| Non-stimulated control[#] | | — | 114<br>109<br>93 | 105 | 6 | 3 | 0 | *** | 100 | 0 | *** |
| Stimulated conditions:<br>PMA - 0.1 µg/ml | Control | — | 2815<br>3230<br>3401 | 3149 | 174 | 100 | 6 | — | 0 | 6 | — |
| | Staurosporine[#] | 10[−9]M | 1579<br>1809<br>1668 | 1685 | 67 | 54 | 2 | ** | 48 | 2 | ** |
| | AM | 0.011 mg/ml | 3210<br>3616<br>2884 | 3237 | 212 | 103 | 7 | ns | −3 | 7 | ns |
| | | 0.033 mg/ml | 2369<br>2377<br>2676 | 2474 | 101 | 79 | 3 | * | 22 | 3 | * |
| | | 0.1 mg/ml | 1658<br>1566<br>1909 | 1711 | 102 | 54 | 3 | ** | 47 | 3 | ** |
| | TM | 0.011 mg/ml | 2740<br>2951<br>3426 | 3039 | 203 | 97 | 6 | ns | 4 | 7 | ns |
| | | 0.033 mg/ml | 2622<br>2355<br>2877 | 2618 | 151 | 83 | 5 | ns | 17 | 5 | ns |

TABLE 8-continued

Evaluation of anti-inflammatory properties through IL-8 release of NHEK stimulated by PMA of AM, TM and SH extracts.

| Treatment | | Basic data | | | | | | Normalized data | | |
|---|---|---|---|---|---|---|---|---|---|---|
| Test compound | Concentration | IL-8 (pg/ml) dilution factor adjusted | Mean (pg/ml) | sem (pg/ml) | % Stimulated control | sem (%) | p[(1)] | % Inhibition | sem (%) | p[(1)] |
| SH | 0.1 mg/ml | 2265 2076 2331 | 2224 | 77 | 71 | 2 | ** | 30 | 3 | ** |
|  | 0.000056 mg/ml | 3363 3288 3515 | 3389 | 67 | 108 | 2 | ns | −8 | 2 | ns |
|  | 0.00017 mg/ml | 3291 3236 3333 | 3287 | 28 | 104 | 1 | ns | −5 | 1 | ns |
|  | 0.0005 mg/ml | 3354 3737 3386 | 3492 | 123 | 111 | 4 | ns | −11 | 4 | ns |

[(1)]Threshold for statistical significance
[#]Non-diluted sample
ns: >0.05, Not significant
*: 0.01 to 0.05, Significant
**: 0.001 to 0.01, Very significant
***: <0.001, Extremely significant

TABLE 9

Migration/proliferation of NHEK of the wound recovery to evaluate cell renewal properties of AM and TM extracts compared to SH extract.

| Test compound | Concentration | # Image | T0 Initial wound area mm² | Wound area mm² | Wound recovery % | 16 hours Mean % | sem % | % Control | p[1] | Wound area mm² | Wound recovery % | 24 hours Mean % | sem % | % Control | p[1] | Wound area mm² | Wound recovery % | 48 hours Mean % | sem % | % Control | p[1] |
|---|---|---|---|---|---|---|---|---|---|---|---|---|---|---|---|---|---|---|---|---|---|
| Control | — | T01 | 3.06 | 1.61 | 47 | 46 | 2 | 100 | — | 1.48 | 52 | 48 | 2 | 100 | — | 1.00 | 67 | 62 | 3 | 100 | — |
|  |  | T02 | 3.01 | 1.86 | 38 |  |  |  |  | 1.81 | 40 |  |  |  |  | 1.34 | 55 |  |  |  |  |
|  |  | T03 | 3.09 | 1.61 | 48 |  |  |  |  | 1.60 | 48 |  |  |  |  | 1.30 | 58 |  |  |  |  |
|  |  | T04 | 3.09 | 1.61 | 48 |  |  |  |  | 1.54 | 50 |  |  |  |  | 1.13 | 63 |  |  |  |  |
|  |  | T05 | 3.13 | 1.53 | 51 |  |  |  |  | 1.44 | 54 |  |  |  |  | 1.05 | 66 |  |  |  |  |
|  |  | T06 | 3.00 | 1.61 | 46 |  |  |  |  | 1.69 | 44 |  |  |  |  | 1.12 | 63 |  |  |  |  |
| EGF | 10 ng/ml | R01 | 3.10 | 0.86 | 72 | 74 | 2 | 159 | *** | 0.64 | 79 | 82 | 2 | 170 | *** | 0.00 | 100 | 100 | 0 | 161 | *** |
|  |  | R02 | 3.12 | 0.69 | 78 |  |  |  |  | 0.44 | 86 |  |  |  |  | 0.01 | 100 |  |  |  |  |
|  |  | R03 | 3.10 | 0.89 | 71 |  |  |  |  | 0.63 | 80 |  |  |  |  | 0.00 | 100 |  |  |  |  |
| AM | 0.011 mg/ml | 13 1 | 3.07 | 1.71 | 44 | 47 | 3 | 102 | ns | 1.61 | 48 | 51 | 3 | 105 | ns | 1.24 | 60 | 60 | 0 | 97 | ns |
|  |  | 13 2 | 2.97 | 1.41 | 53 |  |  |  |  | 1.31 | 56 |  |  |  |  | 1.16 | 61 |  |  |  |  |
|  |  | 13 3 | 2.89 | 1.57 | 46 |  |  |  |  | 1.50 | 48 |  |  |  |  | 1.15 | 60 |  |  |  |  |
|  | 0.033 mg/ml | 12 1 | 2.89 | 1.43 | 51 | 50 | 1 | 107 | ns | 1.40 | 52 | 52 | 1 | 109 | ns | 1.32 | 54 | 56 | 2 | 91 | ns |
|  |  | 12 2 | 2.99 | 1.51 | 49 |  |  |  |  | 1.40 | 53 |  |  |  |  | 1.19 | 60 |  |  |  |  |
|  |  | 12 3 | 2.97 | 1.53 | 48 |  |  |  |  | 1.44 | 52 |  |  |  |  | 1.34 | 55 |  |  |  |  |
|  | 0.1 mg/ml | 11 1 | 3.09 | 2.46 | 20 | 22 | 2 | 48 | *** | 2.37 | 23 | 26 | 1 | 53 | *** | 2.36 | 24 | 28 | 2 | 46 | *** |
|  |  | 11 2 | 2.88 | 2.19 | 24 |  |  |  |  | 2.10 | 27 |  |  |  |  | 2.02 | 30 |  |  |  |  |
|  |  | 11 3 | 3.01 | 2.32 | 23 |  |  |  |  | 2.22 | 26 |  |  |  |  | 2.05 | 32 |  |  |  |  |
| TM | 0.011 mg/ml | 23 1 | 3.09 | 1.02 | 67 | 72 | 3 | 155 | *** | 0.81 | 74 | 79 | 3 | 164 | *** | 0.06 | 98 | 96 | 2 | 154 | *** |
|  |  | 23 2 | 3.06 | 0.73 | 76 |  |  |  |  | 0.61 | 80 |  |  |  |  | 0.26 | 92 |  |  |  |  |
|  |  | 23 3 | 3.25 | 0.88 | 73 |  |  |  |  | 0.58 | 82 |  |  |  |  | 0.09 | 97 |  |  |  |  |
|  | 0.033 mg/ml | 22 1 | 3.04 | 1.32 | 57 | 54 | 3 | 115 | ns | 1.16 | 62 | 59 | 3 | 123 | * | 0.59 | 81 | 80 | 4 | 129 | *** |
|  |  | 22 2 | 2.92 | 1.51 | 48 |  |  |  |  | 1.38 | 53 |  |  |  |  | 0.71 | 76 |  |  |  |  |
|  |  | 22 3 | 3.06 | 1.35 | 56 |  |  |  |  | 1.14 | 63 |  |  |  |  | 0.50 | 84 |  |  |  |  |
|  | 0.1 mg/ml | 21 1 | 3.19 | 1.58 | 50 | 50 | 1 | 108 | ns | 1.45 | 55 | 55 | 0 | 115 | ns | 0.94 | 71 | 73 | 2 | 118 | ** |
|  |  | 21 2 | 3.13 | 1.60 | 49 |  |  |  |  | 1.41 | 55 |  |  |  |  | 0.71 | 77 |  |  |  |  |
|  |  | 21 3 | 3.10 | 1.51 | 51 |  |  |  |  | 1.39 | 55 |  |  |  |  | 0.85 | 73 |  |  |  |  |
| SH | 0.011 mg/ml | 43 1 | 3.19 | 1.76 | 45 | 41 | 3 | 87 | ns | 1.69 | 47 | 44 | 1 | 93 | ns | 1.48 | 54 | 55 | 1 | 88 | * |
|  |  | 43 2 | 3.21 | 1.87 | 42 |  |  |  |  | 1.79 | 44 |  |  |  |  | 1.42 | 56 |  |  |  |  |
|  |  | 43 3 | 3.12 | 2.03 | 35 |  |  |  |  | 1.81 | 42 |  |  |  |  | 1.40 | 55 |  |  |  |  |
|  | 0.033 mg/ml | 42 1 | 3.01 | 1.58 | 48 | 45 | 2 | 97 | ns | 1.42 | 53 | 51 | 2 | 106 | ns | 0.95 | 68 | 66 | 3 | 106 | ns |
|  |  | 42 2 | 3.08 | 1.61 | 48 |  |  |  |  | 1.42 | 54 |  |  |  |  | 0.90 | 71 |  |  |  |  |
|  |  | 42 3 | 3.08 | 1.83 | 41 |  |  |  |  | 1.66 | 46 |  |  |  |  | 1.25 | 59 |  |  |  |  |
|  | 0.1 mg/ml | 41 1 | 3.07 | 1.47 | 52 | 46 | 4 | 100 | ns | 1.34 | 56 | 52 | 5 | 108 | ns | 0.80 | 74 | 69 | 4 | 111 | ns |
|  |  | 41 2 | 3.07 | 1.61 | 48 |  |  |  |  | 1.35 | 56 |  |  |  |  | 0.84 | 73 |  |  |  |  |
|  |  | 41 3 | 3.09 | 1.86 | 40 |  |  |  |  | 1.78 | 42 |  |  |  |  | 1.19 | 61 |  |  |  |  |

[1]Threshold for statistical significance
ns: >0.05, Not significant
*: 0.01 to 0.05, Significant
**: 0.001 to 0.01, Very significant
***: <0.001, Extremely significant

TABLE 10

| | | Wound recovery (mean value) at different concentrations C1-C3 (0.1, 0.03 and 0.01 mg/mL) | | |
|---|---|---|---|---|
| | | Incubation time (hours) | | |
| | | 16 | 24 | 48 |
| AM | C1 | 47% | 51% | 60% |
| | C2 | 50% | 52% | 52% |
| | C3 | 22% | 26% | 28% |
| TM | C1 | 72% | 79% | 96% |
| | C2 | 54% | 59% | 80% |
| | C3 | 55% | 55% | 73% |

TABLE 11

| | | Hyaluronic acid synthesis | | | | | | | | |
|---|---|---|---|---|---|---|---|---|---|---|
| | | | Basic data | | | | | | Normalized data | |
| Treatment | | Hyaluronic acid (ng/ml) | | | | | | | | |
| Test compound | Concentration | dilution factor adjusted | Mean (ng/ml) | sem (ng/ml) | % Control | sem (%) | $p^{(1)}$ | % Stimulation | sem (%) | $p^{(1)}$ |
| Control | — | 263.5 | 272.1 | 19.8 | 100 | 7 | — | 0 | 7 | — |
| | | 309.9 | | | | | | | | |
| | | 243.0 | | | | | | | | |
| Retinoic acid | $10^{-7}$M | 677.2 | 655.7 | 13.1 | 241 | 5 | *** | 141 | 5 | *** |
| | | 632.1 | | | | | | | | |
| | | 657.9 | | | | | | | | |
| AM | 0.011 mg/ml | 296.1 | 293.9 | 3.8 | 108 | 1 | ns | 8 | 1 | ns |
| | | 299.0 | | | | | | | | |
| | | 286.5 | | | | | | | | |
| | 0.033 mg/ml | 275.3 | 303.6 | 16.5 | 112 | 6 | ns | 12 | 6 | ns |
| | | 303.1 | | | | | | | | |
| | | 332.4 | | | | | | | | |
| | 0.1 mg/ml | 279.4 | 314.0 | 17.4 | 115 | 6 | ns | 15 | 6 | ns |
| | | 333.8 | | | | | | | | |
| | | 328.8 | | | | | | | | |
| TM | 0.011 mg/ml | 268.8 | 273.0 | 4.2 | 100 | 2 | ns | 0 | 2 | ns |
| | | 281.3 | | | | | | | | |
| | | 268.8 | | | | | | | | |
| | 0.033 mg/ml | 290.3 | 331.8 | 21.4 | 122 | 8 | ns | 22 | 8 | ns |
| | | 343.9 | | | | | | | | |
| | | 361.3 | | | | | | | | |
| | 0.1 mg/ml | 313.3 | 289.5 | 18.2 | 106 | 7 | ns | 6 | 7 | ns |
| | | 253.8 | | | | | | | | |
| | | 301.3 | | | | | | | | |
| SH | 0.011 mg/ml | 219.4 | 253.5 | 19.4 | 93 | 7 | ns | −7 | 7 | ns |
| | | 254.4 | | | | | | | | |
| | | 286.8 | | | | | | | | |
| | 0.033 mg/ml | 295.7 | 276.6 | 18.8 | 102 | 7 | ns | 2 | 7 | ns |
| | | 295.1 | | | | | | | | |
| | | 239.0 | | | | | | | | |
| | 0.1 mg/ml | 270.8 | 272.4 | 8.4 | 100 | 3 | ns | 0 | 3 | ns |
| | | 287.8 | | | | | | | | |
| | | 258.7 | | | | | | | | |

The foregoing is illustrative of the present invention, and is not to be construed as limiting thereof. The invention is defined by the following claims, with equivalents of the claims to be included therein.

We claim:

1. A skin formulation consisting essentially of an extract from the leaves and/or the stems of *Arthrocnemum macrostachyum* and *Tetraena* sp. Cf. *mandavilie* and an emulsifier.

* * * * *